(12) United States Patent
Wang

(10) Patent No.: US 8,858,513 B2
(45) Date of Patent: Oct. 14, 2014

(54) DISPOSABLE INTRAVENOUS FLOW CONTROL DEVICE

(75) Inventor: Hsien-Tsung Wang, Taipei (TW)

(73) Assignee: Dragon Heart Medical Devices Co., Ltd., Kaiping, Guangdong Province (CN)

( * ) Notice: Subject to any disclaimer, the term of this patent is extended or adjusted under 35 U.S.C. 154(b) by 747 days.

(21) Appl. No.: 13/067,187

(22) Filed: May 16, 2011

(65) Prior Publication Data

US 2012/0296288 A1 Nov. 22, 2012

(51) Int. Cl.
 *A61M 5/14* (2006.01)
 *A61M 5/168* (2006.01)
 *A61M 5/40* (2006.01)
 *A61M 5/00* (2006.01)

(52) U.S. Cl.
 CPC ............ *A61M 5/00* (2013.01); *A61M 5/16804* (2013.01); *A61M 5/40* (2013.01); *A61M 5/1411* (2013.01)
 USPC .......................................................... 604/254

(58) Field of Classification Search
 USPC ................................................. 604/251–256
 See application file for complete search history.

(56) References Cited

U.S. PATENT DOCUMENTS

| | | | | |
|---|---|---|---|---|
| 3,216,419 A * | 11/1965 | Scislowicz | ................... | 604/127 |
| 3,227,173 A * | 1/1966 | Bernstein | ...................... | 137/192 |
| 4,078,563 A * | 3/1978 | Tuseth | ........................... | 604/127 |
| 4,395,260 A * | 7/1983 | Todd et al. | ..................... | 604/122 |
| 4,769,012 A * | 9/1988 | Quang et al. | .................. | 604/247 |
| 5,031,654 A * | 7/1991 | Kobayashi | ..................... | 137/192 |
| 5,415,325 A * | 5/1995 | Shu | .................................... | 222/66 |
| 5,423,346 A * | 6/1995 | Daoud | .......................... | 137/399 |
| 5,569,208 A * | 10/1996 | Woelpper et al. | ............. | 604/183 |
| 5,730,730 A * | 3/1998 | Darling, Jr. | .................... | 604/246 |
| 5,868,715 A * | 2/1999 | Tung | .............................. | 604/256 |
| 6,213,986 B1 * | 4/2001 | Darling, Jr. | ................... | 604/248 |
| 6,569,116 B1 * | 5/2003 | Wang | ............................. | 604/127 |
| 6,641,559 B2 * | 11/2003 | Guala | ........................... | 604/127 |
| 6,695,004 B1 * | 2/2004 | Raybuck | ....................... | 137/433 |
| 7,731,699 B2 * | 6/2010 | Mottola | ......................... | 604/254 |
| 7,879,014 B2 * | 2/2011 | Mottola | ......................... | 604/254 |
| 8,328,770 B2 * | 12/2012 | Wang | ............................. | 604/254 |
| D675,729 S * | 2/2013 | Wang | ............................. | D24/108 |
| 8,439,880 B2 * | 5/2013 | Rondeau | ....................... | 604/256 |
| D683,842 S * | 6/2013 | Wang | ............................. | D24/108 |
| 8,480,635 B2 * | 7/2013 | Wang et al. | .................... | 604/254 |
| 8,568,368 B2 * | 10/2013 | Lampropoulos et al. | ..... | 604/246 |

* cited by examiner

*Primary Examiner* — Kevin C Sirmons
*Assistant Examiner* — William Carpenter
(74) *Attorney, Agent, or Firm* — Jackson IPG PLLC

(57) ABSTRACT

A disposable intravenous flow control device (20) includes a rigid casing (21) defining a flow passage having a fluid entrance (23) and a fluid exit (22); a flow regulator (10) disposed in the flow passage of the casing (21) and comprising an annular flange (11) extending upward, a hollow, cylindrical protrusion (12) raised upward from a central portion, the protrusion (12) being open to the bottom, an open fluid storage (13) defined between the flange (11) and the protrusion (12), and a hollow, cylindrical skirt (14) extending downward from the bottom of the protrusion (12); and a suction cup (15) releasably secured to the skirt (14) for blocking the fluid exit (22) when fluid in the casing (21) is consumed.

8 Claims, 16 Drawing Sheets

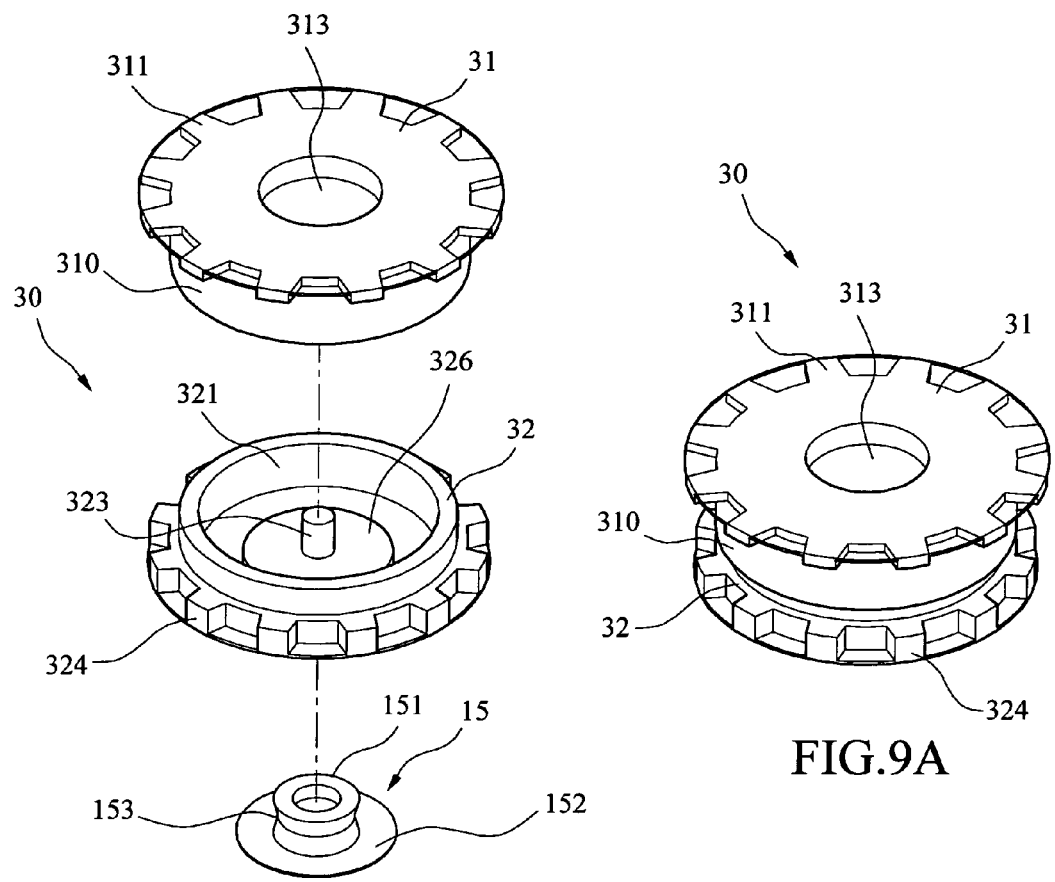
FIG.9
FIG.9A
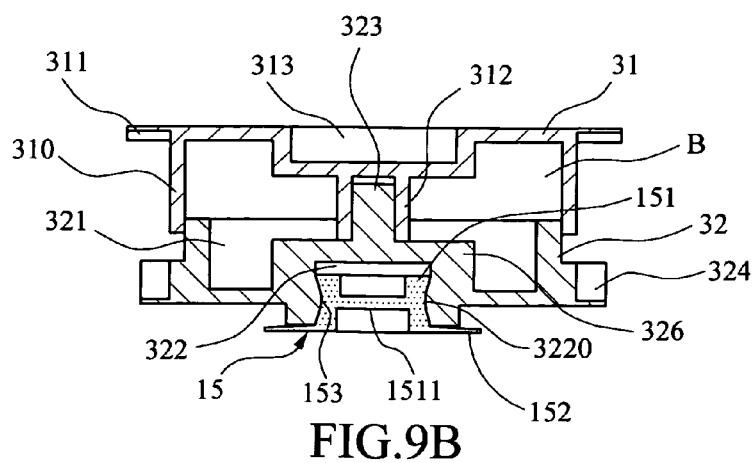
FIG.9B

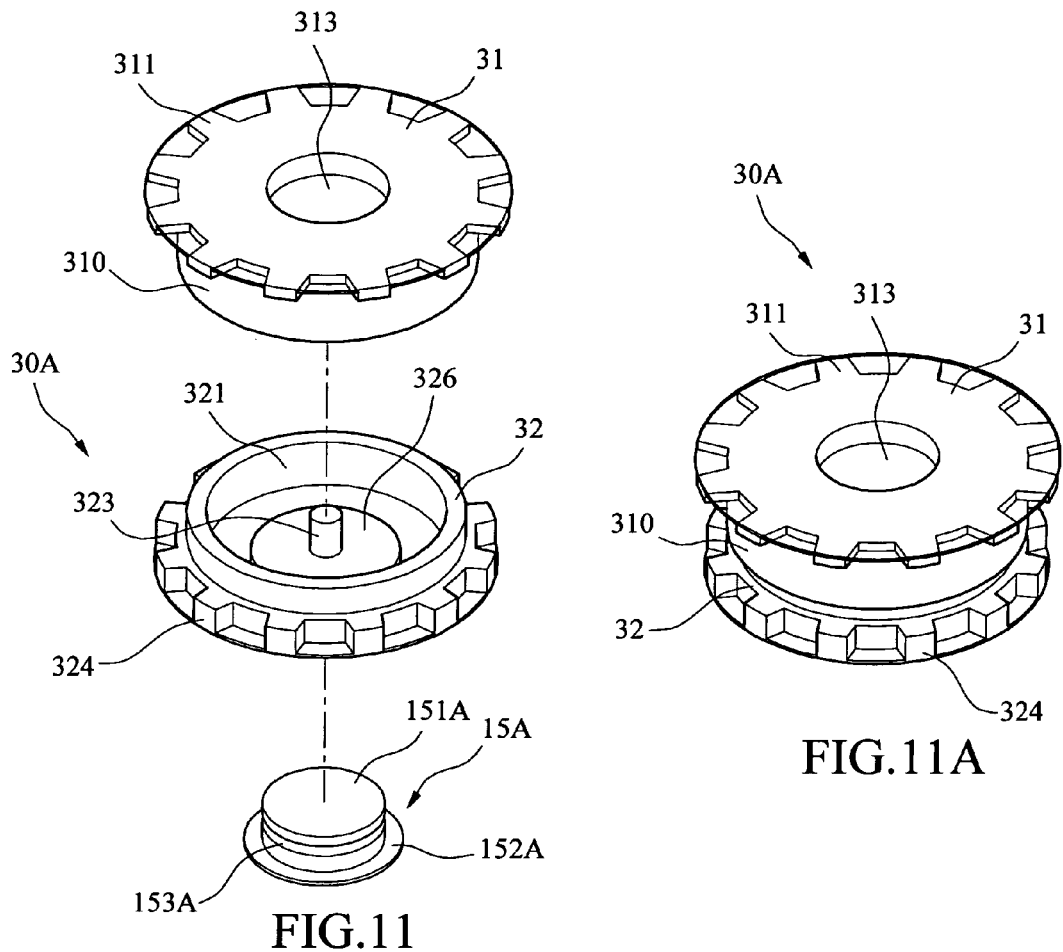
FIG.11
FIG.11A
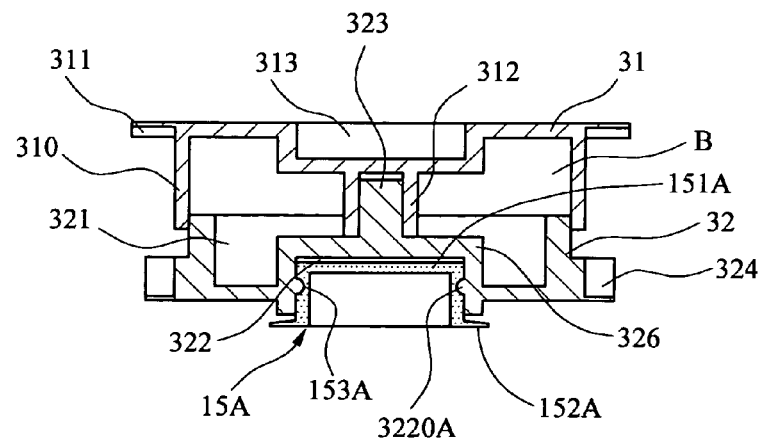
FIG.11B

DISPOSABLE INTRAVENOUS FLOW CONTROL DEVICE

BACKGROUND OF THE INVENTION

1. Field of the Invention

The invention relates to intravenous (IV) fluid flow control and more particularly to a disposable intravenous flow control device with improved characteristics.

2. Description of Related Art

IV flow control devices are well known. For example, a typical IV flow control device 20T as a part of an IV infusion set is shown in FIG. 15. The IV flow control device 20T comprises a rigid casing filled with fluid and a disk shaped valve 90 moveably floated therein. The valve 90 has a central through hole (not shown). A membrane (not shown) is provided on a fluid exit of the casing. The valve 90 has a diameter smaller than an inner diameter of the casing so that the valve 90 may move toward an upstream fluid entrance as fluid flows into the casing or may move toward the exit as the fluid exits as known in the art.

However, the casing may be inclined when fluid is dispensing to a patient. Thus, the valve 90 may rotate clockwise or counterclockwise as indicated by phantom line outlines. As a result, the desired fluid control mechanism is compromised because the membrane may not work normally to exit fluid. Thus, the need for improvement still exists.

SUMMARY OF THE INVENTION

It is therefore one object of the invention to provide a disposable intravenous flow control device comprising a flow regulator which may rotate clockwise and counterclockwise repeatedly the casing is inclined. It is advantageously that both the top end of the riser and the edge of the flange may contact an inner surface of the casing to stop the rotation. Thus, the rotation is limited to a predetermined angle without compromising the normal fluid control mechanism of the flow regulator, thereby maintaining a normal fluid exit.

Another object of the invention to provide a disposable intravenous flow control device wherein an annular member of the flow regulator is tightly engaged with the casing bottom due to the weight of the fluid accumulated in the fluid storage and the fluid exit is completely blocked by the suction cup due to complimentary shapes when the fluid is completely consumed at the end of an intravenous injection. This is a double fluid blocking mechanism of the invention.

To achieve above and other objects, the invention provides a disposable intravenous flow control device comprising a rigid casing defining a flow passage having a fluid entrance and a fluid exit; a flow regulator disposed in the flow passage of the casing and comprising an annular flange extending upward, a hollow, cylindrical protrusion raised upward from a central portion, the protrusion being open to the bottom, an open fluid storage defined between the flange and the protrusion, and a hollow, cylindrical skirt extending downward from the bottom of the protrusion; and a suction cup releasably secured to the skirt for blocking the fluid exit when fluid in the casing is consumed.

To achieve above and other objects, the invention further provides a disposable intravenous flow control device comprising a rigid casing defining a flow passage having a fluid entrance and a fluid exit; a flow regulator disposed in the flow passage of the casing and comprising a disc-shaped upper float member including a bottom outer rim, a plurality of equally spaced teeth along an annular top edge, and a bottom inner rim; and a disc-shaped lower float member including an annular flange adjacent to edge and extending upward, a solid cylinder on the center of a top hollow riser, a plurality of equally spaced teeth along edge and below the flange, and a hollow cylindrical skirt extending downward from the hollow riser wherein the cylinder is fitted in the inner rim to secure the upper and lower float members together, and the outer rim is securely engaged around the flange so as to define a closed space in the flow regulator; and a suction cup releasably secured to the skirt for blocking the fluid exit when fluid in the casing is consumed.

Preferably, the suction cup comprises a central, hollow projection extending upward, a separation member for separating an internal space of the projection into upper and lower portions, an annular groove on an intermediate portion of an outer surface of the projection, and an annular member on the bottom.

Preferably, the suction cup further comprises a flat top surface, an annular groove below the top surface, and an annular extension member descending downward from the bottom of the groove.

Preferably, the suction cup further comprises a flat top surface lockingly fitted in the skirt, an annular groove below the top surface, and a flared member descending downward from the groove, and wherein the top surface has a thickness greater than that of the flared member.

Preferably, buoyancy of the flow regulator together with the suction cup is slightly greater than the gravity force coming from the weight of fluid contained in the circular fluid storage, the specific weight of the flow regulator and the suction cup is about 0.8 to 1.0; and capacity of the fluid storage is devised to be an optimum by taking the specific gravity of the fluid to be dispensed by the IV flow control device into consideration.

Preferably, buoyancy of the upper float member is slightly greater than that of both the lower float member and the suction cup, the specific weight of the flow regulator is about 0.8 to 1.0; capacities of the fluid storage and that of a closed space B defined by the outer rim tightly engaged around an upper portion of the flange are devised to be an optimum by taking the specific gravity of the fluid to be dispensed by the IV flow control device into consideration.

The above and other objects, features and advantages of the invention will become apparent from the following detailed description taken with the accompanying drawings.

BRIEF DESCRIPTION OF THE DRAWINGS

FIG. 9 is an exploded perspective view of a flow regulator as a part of a disposable intravenous flow control device according to a fourth preferred embodiment of the invention;

FIG. 9A is a perspective view of the assembled flow regulator of FIG. 9;

FIG. 9B is a longitudinal sectional view of the flow regulator of FIG. 9A;

FIG. 11 is an exploded perspective view of a flow regulator as a part of a disposable intravenous flow control device according to a fifth preferred embodiment of the invention;

FIG. 11A is a perspective view of the assembled flow regulator of FIG. 11;

FIG. 11B is a longitudinal sectional view of the flow regulator of FIG. 11A;

DETAILED DESCRIPTION OF THE INVENTION

Referring to FIGS. 1 to 6, a disposable intravenous flow control device 20 in accordance with a first preferred embodiment of the invention comprises the following components as discussed in detail below.

Figure 5:
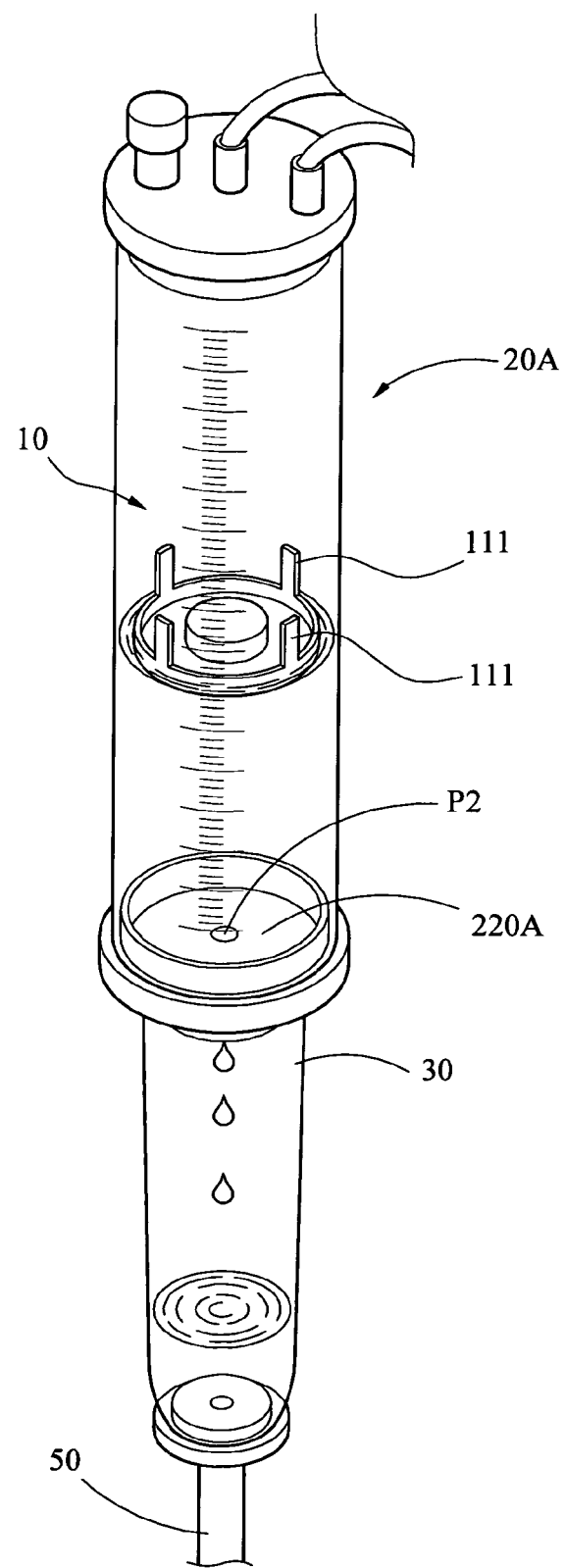
FIG. 5 is a perspective view of the IV flow control device with the flow regulator moveably disposed therein when fluid is filled in the casing of the IV flow control device and both a chamber and a tube being mounted therewith.
Figure 5A:
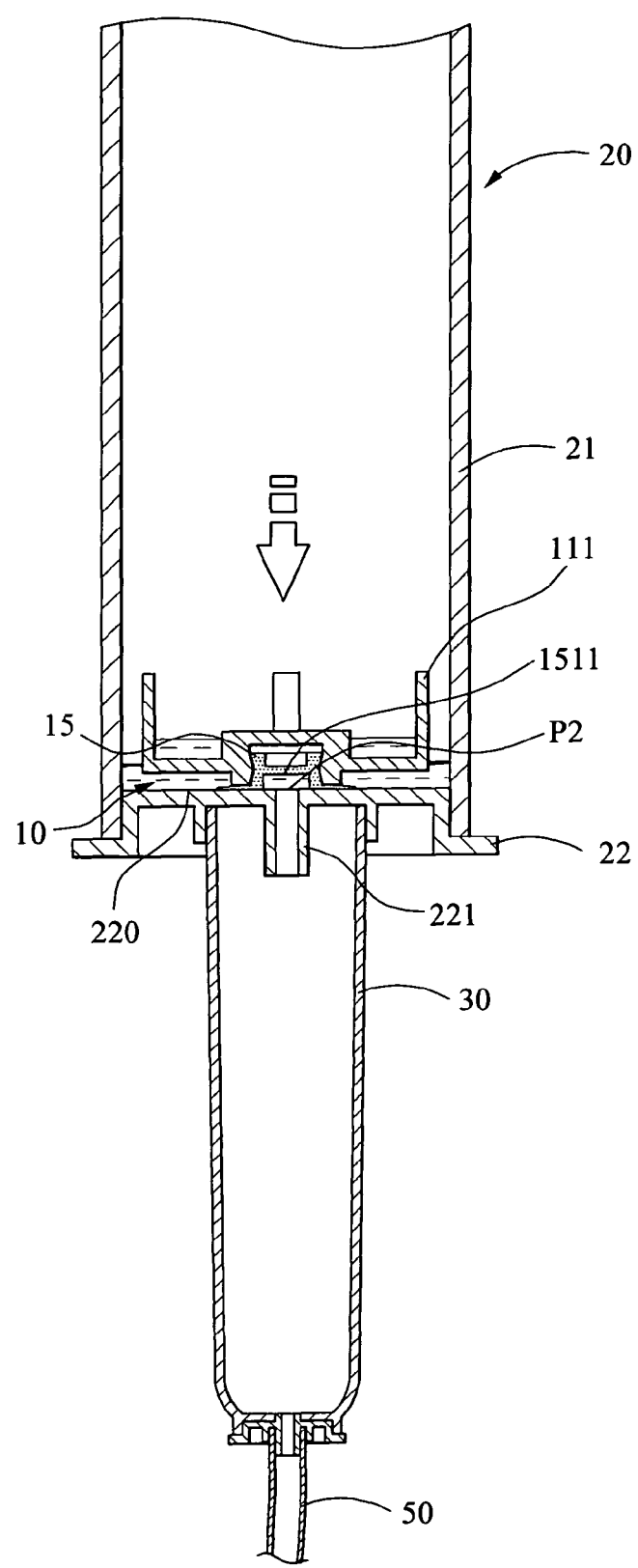
FIG. 5A is a longitudinal sectional view of most portions of FIG. 5 showing fluid being completely consumed and the flow regulator falling onto the fluid exit to stop the flow.
Figure 5B:
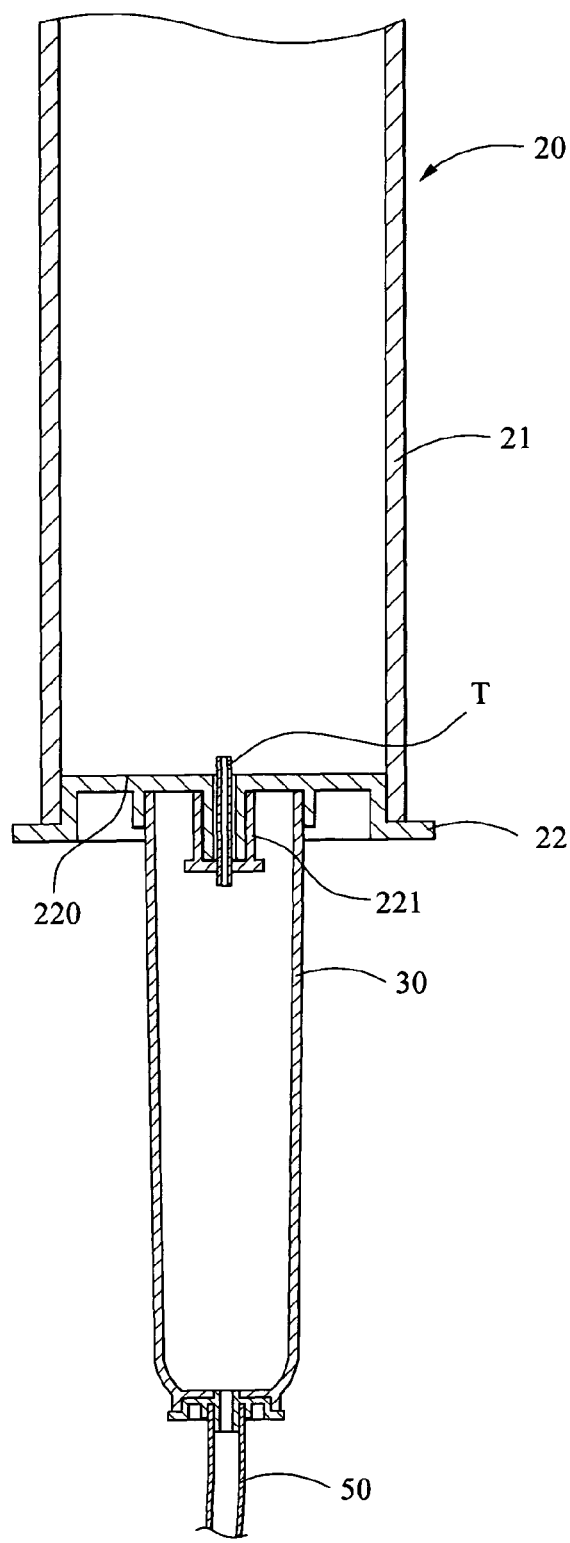
FIG. 5B is a view similar to FIG. 5A with the flow regulator removed and a plug inserted into the exit for blocking purpose.

A cylindrical casing 21 is rigid and transparent in nature. The casing 21 defines a flow passage having a top fluid entrance 23 and a bottom protrusion fluid exit P1 implemented by an outlet member 22. The outlet member 22 comprises a raised top 220 and a short, hollow cylinder 221 having a projecting top end 221a open to the top 220 and a bottom end 221b open to a chamber 30 secured thereto. A tube 50 is secured to an open end of the chamber 30 distal the cylinder 221. The cylinder 221 can define as a protrusion fluid exit path P1 (see FIGS. 2-4) or a flat fluid exit path P2 (see FIG. 5, 5A) at a joining point with the top 220. The cylinder 221 can also be reduced its inner diameter by inserting a plug tube T thereinto (see FIG. 5B).

Figure 1:
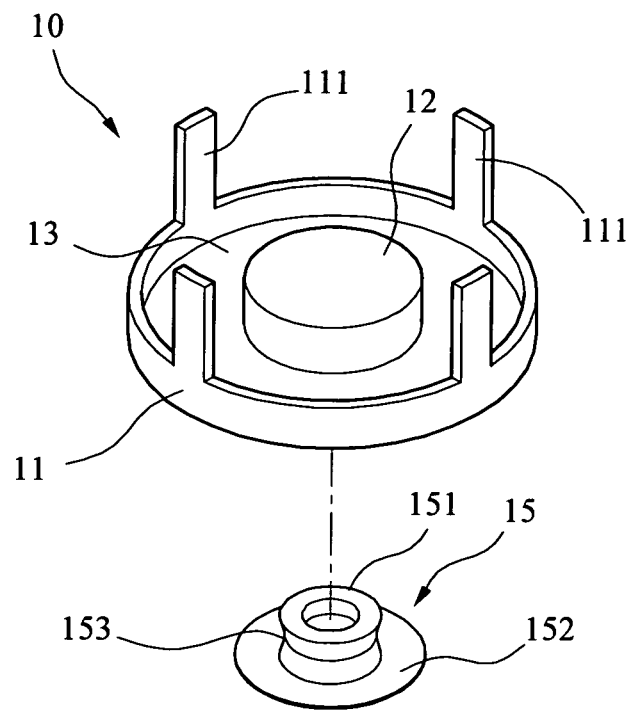
FIG. 1 is an exploded perspective view of a flow regulator as a part of a disposable intravenous flow control device according to a first preferred embodiment of the invention.
Figure 1A:
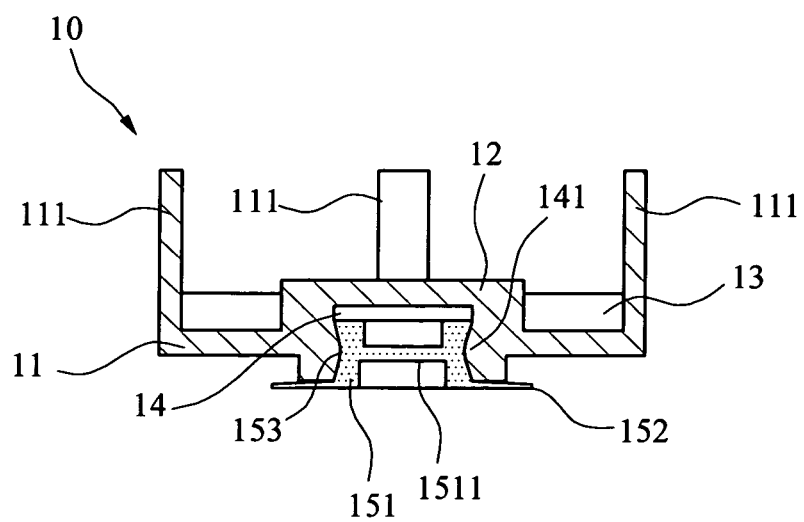
FIG. 1A is a longitudinal sectional view of the assembled flow regulator of FIG. 1.
Figure 2:
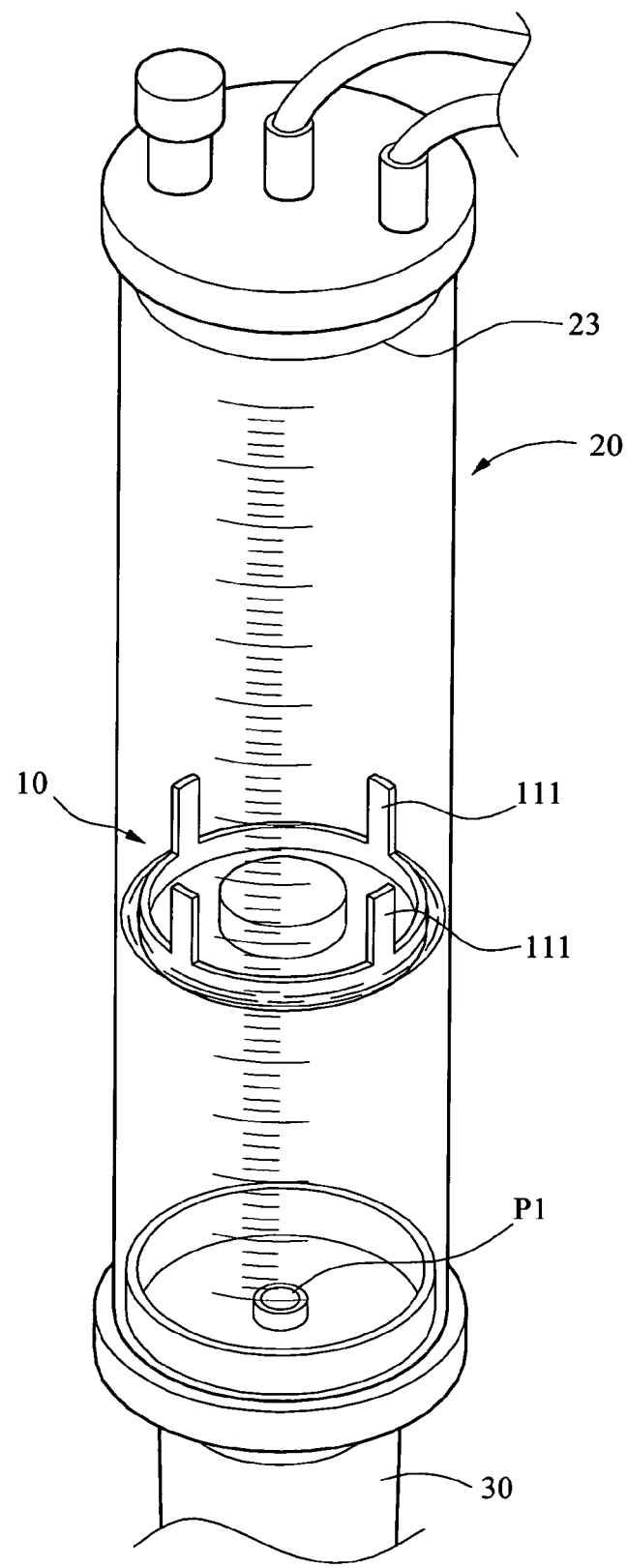
FIG. 2 is a perspective view of the IV flow control device with the flow regulator moveably disposed therein when fluid is filled in the casing of the IV flow control device.
Figures 3, 4:
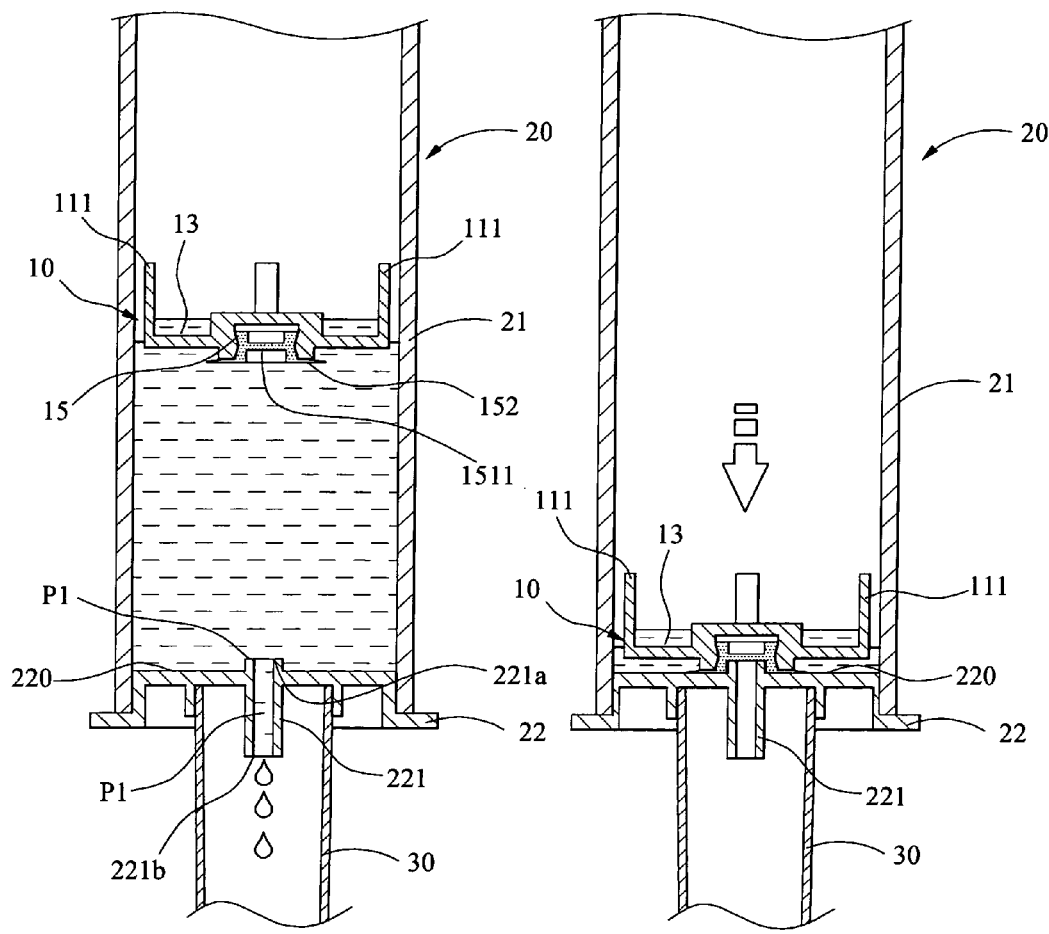
FIG. 3 is a longitudinal sectional view of the intermediate and lower portions of the IV flow control device of FIG. 2 with fluid being exited.
FIG. 4 is a view similar to FIG. 3 showing fluid being completely consumed and the flow regulator falling onto the fluid exit to stop the flow.

A flow regulator 10 is shaped as a disc and comprises an annular flange 11 extending upward, four equally spaced risers 111 projecting upward from a top edge of the flange 11, a cylindrical protrusion 12 raised upward from a central portion, the protrusion 12 being hollow, an open fluid storage 13 defined between the flange 11 and the protrusion 12, and a hollow, cylindrical skirt 14 extending downward a short distance from the hollow of the protrusion 12, the skirt 14 having an annular neck 141 in an intermediate portion and being substantially flush with the bottom of the flange 11. The neck 141 has smooth upper and lower slopes as seen from FIG. 1A.

A suction cup 15 comprises a central, hollow projection 151 extending upward and having a separation member 1511 for separating the internal space of the projection 151 into upper and lower portions wherein the height of the separation member 1511 can be varied in accordance with the projecting length of the top end 221a so as to completely cover the whole length of the top end 221a opening to the top 220, an annular groove 153 on an intermediate portion of an outer surface of the projection 151, and an annular extension member 152 on the bottom. The bottom of the flange 11, the groove 153, and the separation member 1511 are substantially flush. The projection 151 has a longitudinal section of H (see FIG. 1A). The suction cup 15 can be complimentarily fastened in the skirt 14 with the neck 141 lockingly engaged with the groove 153 and the bottom of the skirt 14 engaged with the annular extension member 152.

As shown in FIGS. 3 to 5B, the flow regulator 10 has an outer diameter smaller than an inner diameter of the casing 21 so that the flow regulator 10 may float in the casing 21 when fluid entering the casing 21. The flow regulator 10 may axially move, for example, downward in the casing 21 as fluid continues to flow into the chamber 30 via the fluid exit path P1. The annular extension member 152 is tightly engaged with the top 220 due to the weight of the fluid accumulated in the fluid storage 13 and the top end 221a is completely blocked by the hollow bottom portion of the projection 151 due to complimentary shapes when the fluid is completely consumed at the end of an IV injection. This is a double fluid blocking mechanism of the invention.

Buoyancy of the flow regulator 10 together with the suction cup 15 is slightly greater than the gravity force coming from the weight of fluid contained in the circular fluid storage 13, the specific weight of the flow regulator 10 and the suction cup 15 is about 0.8 to 1.0, preferably, the specific weight is of 0.9 and capacity of the fluid storage 13 is devised to be an optimum by taking the specific gravity of the fluid to be dispensed by the IV flow control device 20 into consideration.

Figure 6:
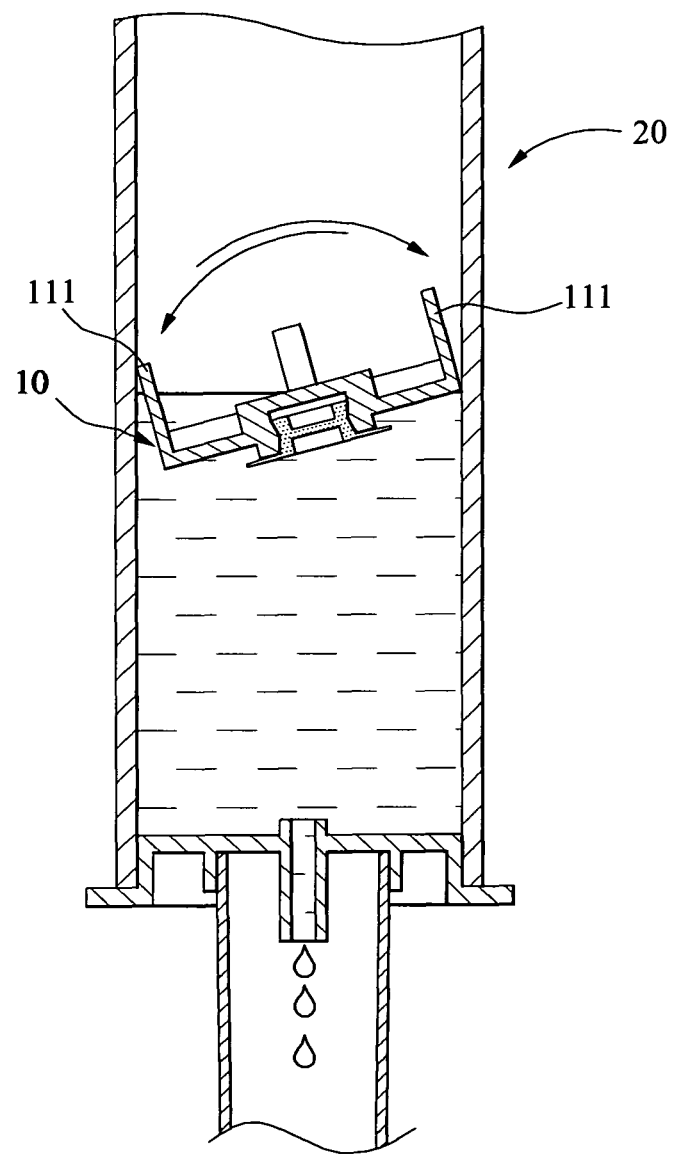
FIG. 6 is a view similar to FIG. 3 showing the flow regulator being rotated clockwise and counterclockwise in response to vibrating the casing of the IV flow control device or an inclined position thereof.

Moreover, as shown in FIG. 6, the flow regulator 10 may rotate clockwise and counterclockwise repeatedly as indicated by arrows when the casing 21 is inclined. It is advantageously that both the top end of the riser 111 and the edge of the flange 11 may contact the inner surface of the casing 21 to stop the rotation. Thus, the rotation is limited to a predetermined angle without compromising the normal fluid flow (or fluid control mechanism) of the flow regulator 10. As a result, the fluid exit can be maintained normally.

Figure 7:
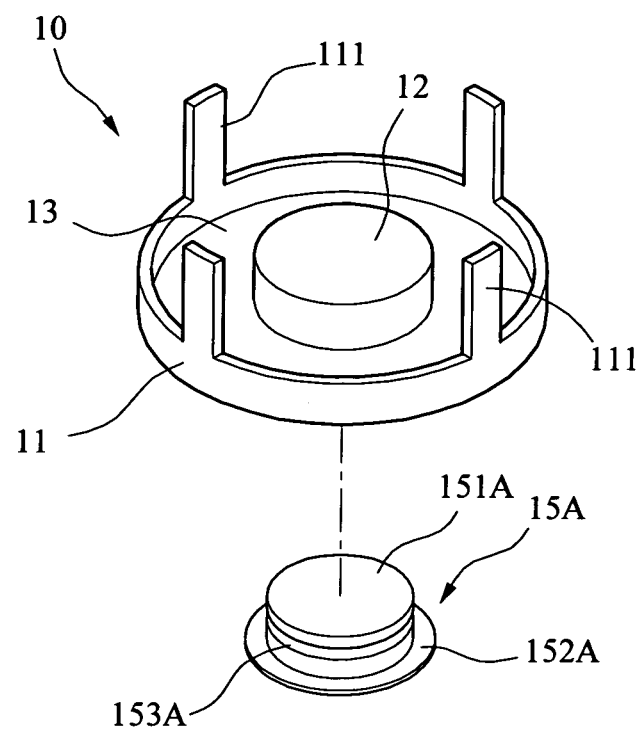
FIG. 7 is an exploded perspective view of a flow regulator as a part of a disposable intravenous flow control device according to a second preferred embodiment of the invention.
Figure 7A:
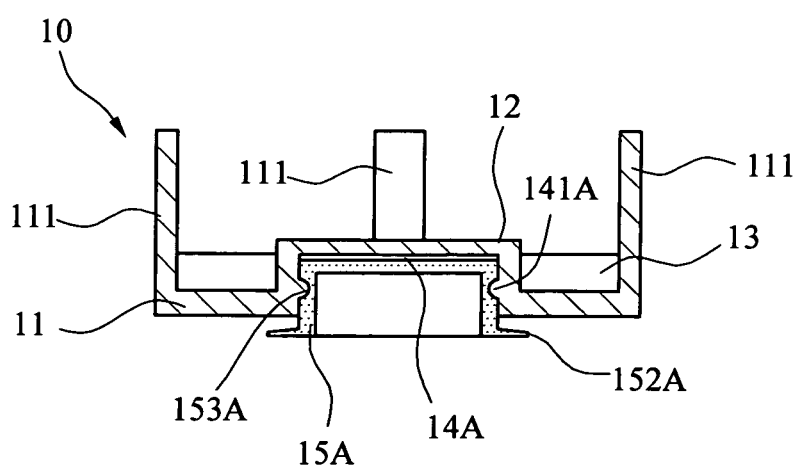
FIG. 7A is a longitudinal sectional view of the assembled flow regulator of FIG. 7.

Referring to FIGS. 7 and 7A, a disposable intravenous flow control device in accordance with a second preferred embodiment of the invention is shown. The characteristics of the second preferred embodiment are substantially the same as that of the first preferred embodiment except the following:

The separation member is eliminated. The top of the suction cup 15A is a flat surface 151A. The neck 141A has a convex longitudinal section and the groove 153A has a concave longitudinal section. The neck 141A and the groove 153A can be complementarily engaged together. Bottom of the flow regulator 10 is flat. Further, there is a distance between the annular extension member 152A and the bottom of the flow regulator 10 when the flow regulator 10 and the suction cup 15A are secured together.

Figure 8:
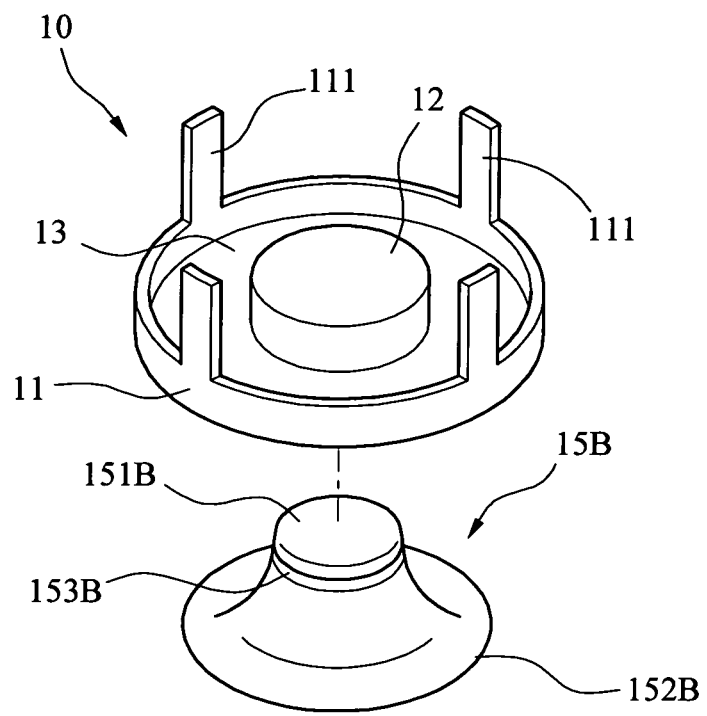
FIG. 8 is an exploded perspective view of a flow regulator as a part of a disposable intravenous flow control device according to a third preferred embodiment of the invention.
Figure 8A:
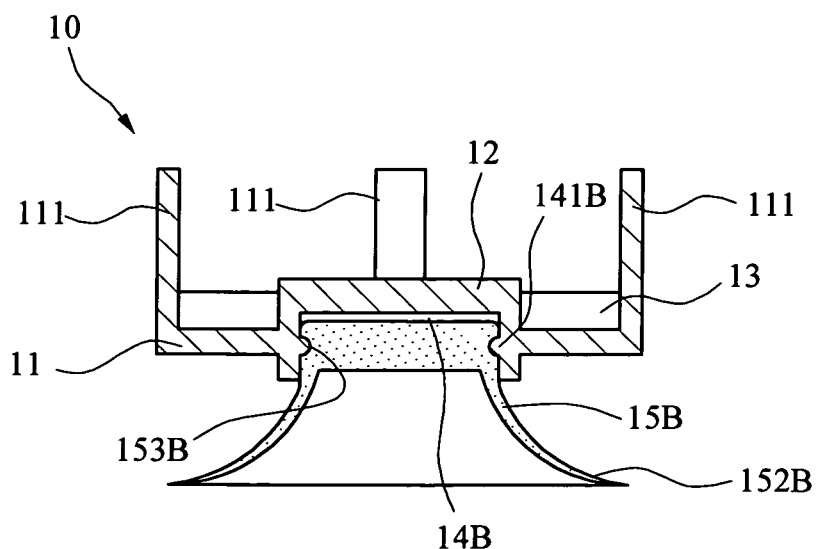
FIG. 8A is a longitudinal sectional view of the assembled flow regulator of FIG. 8.

Referring to FIGS. 8 and 8A, a disposable intravenous flow control device in accordance with a third preferred embodiment of the invention is shown. The characteristics of the third preferred embodiment are substantially the same as that of the second preferred embodiment (i.e., a flat top surface 151A and an annular groove 153A) except the following: Bottom of the flow regulator 10 has an annular projecting rim. The suction cup 15B has a flared member 152B. The top surface 151B has a thickness greater than that of the flared member 152B.

Figure 10:
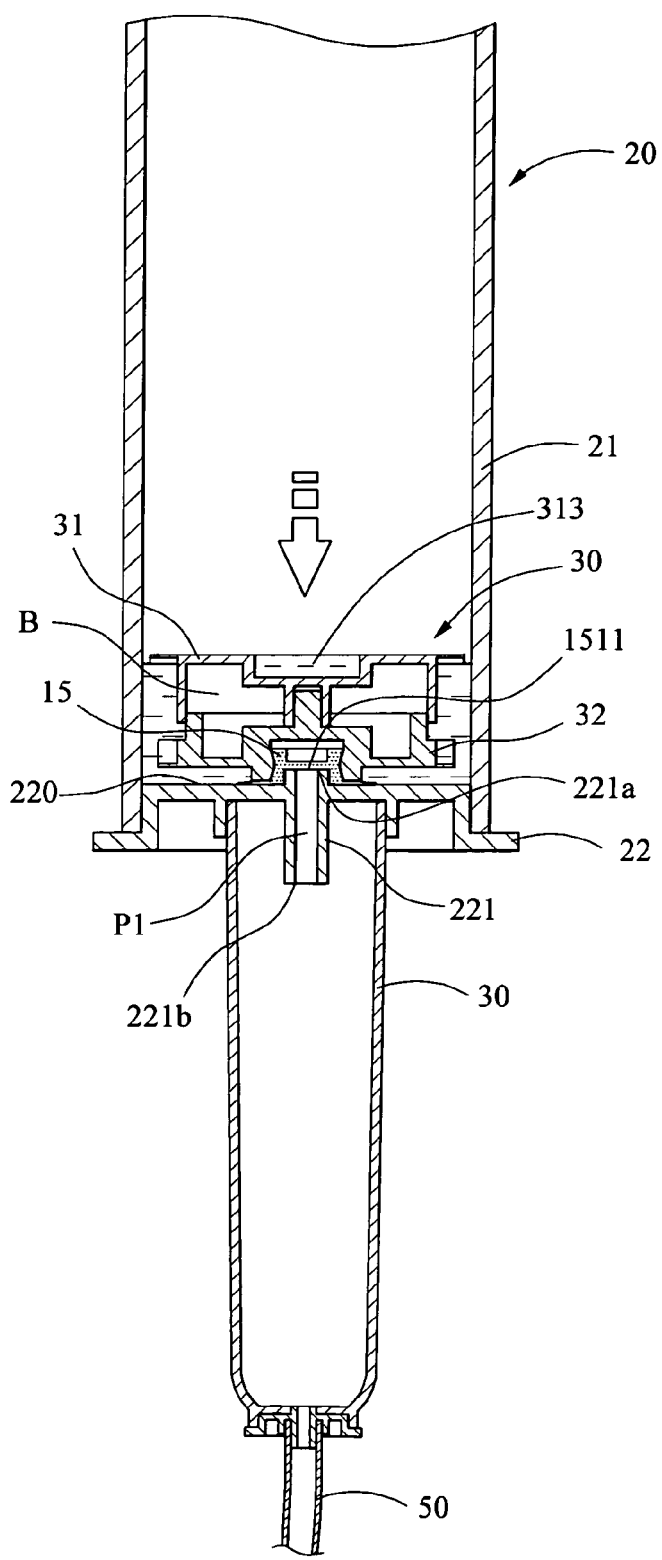
FIG. 10 is a view similar to FIG. 5A showing fluid being completely consumed and the flow regulator of FIG. 9B falling onto the fluid exit to stop the flow.

Referring to FIGS. 9 to 10, a disposable intravenous flow control device in accordance with a fourth preferred embodiment of the invention is shown. The characteristics of the fourth preferred embodiment are substantially the same as that of the first preferred embodiment except the following: The flow regulator 30 comprises a disc-shaped upper float member 31 including a bottom outer rim 310, a circular open fluid storage 313 on a top center, a plurality of equally spaced teeth 311 along an annular top edge, and a bottom inner rim 312 extending downward from the underside of the fluid storage 313; and a disc-shaped lower float member 32 including an annular flange 321 adjacent to edge and extending upward, a solid cylinder 323 on the center of a hollow riser 326 of top, a plurality of equally spaced teeth 324 along edge and below the flange 321, and a hollow, cylindrical skirt 322 extending downward a short distance from the hollow of the riser 326, the skirt 322 having an annular neck 3220 in an intermediate portion and being substantially flush with the bottom of the teeth 324. The neck 3220 has smooth upper and lower slopes. The cylinder 323 can be fitted in the inner rim 312 to secure the upper and lower float members 31, 32 together. Further, the outer rim 310 is tightly engaged around an upper portion of the flange 321 so as to define a closed space B in the flow regulator 30. The suction cup 15 can be mounted in the skirt 322 the same as that described in the first preferred embodiment.

Buoyancy of the upper float member 31 is slightly greater than that of both the lower float member 32 and the suction cup 15. Preferably, the specific weight of the flow regulator 30 is defined about 0.8 to 1.0, preferably, the specific weight is of 0.9. The capacities of the fluid storage 313 and that of the closed space defined by the flange 321 are devised to be an optimum by taking the specific gravity of the fluid to be dispensed by the IV flow control device into consideration.

Figure 12:
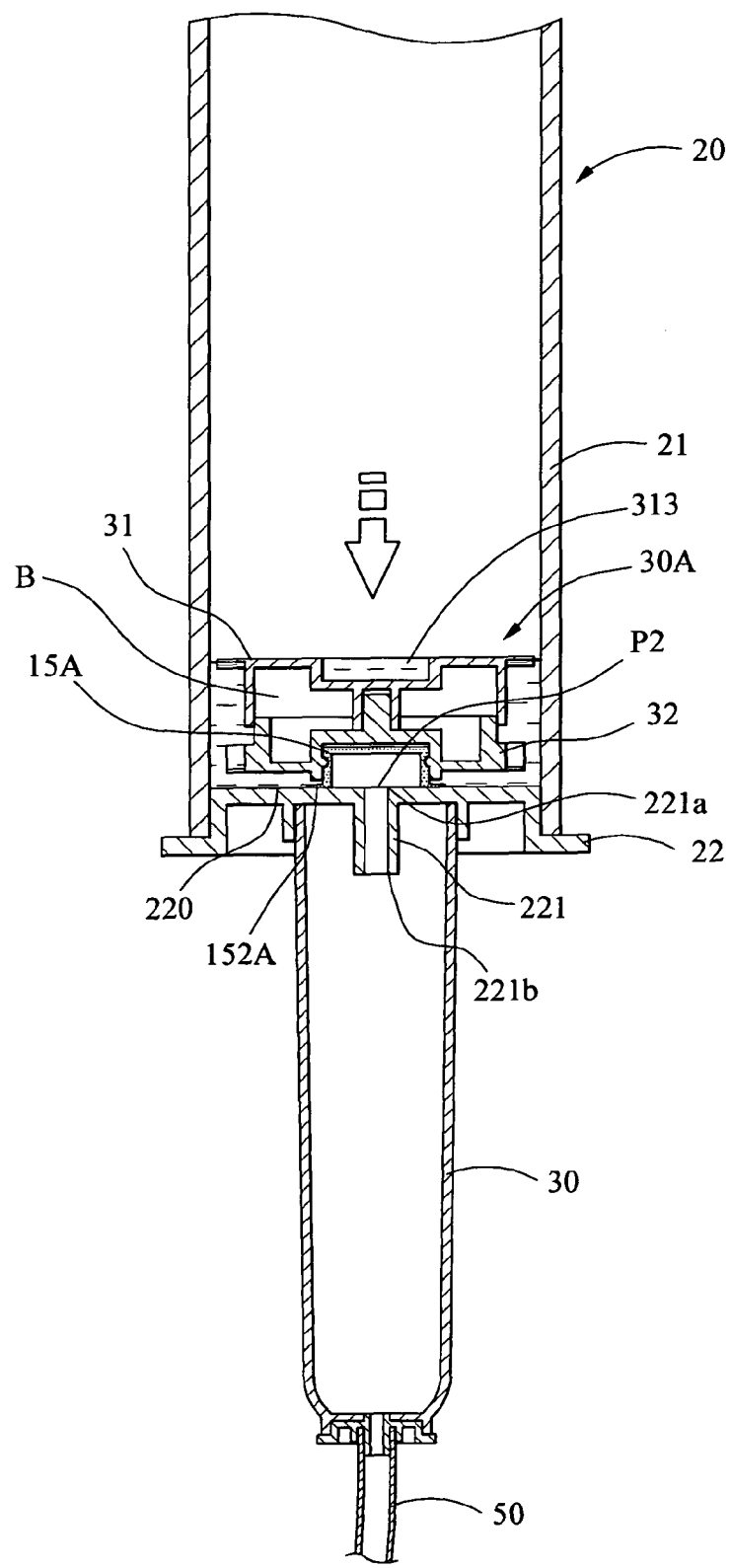
FIG. 12 is a view similar to FIG. 5A showing fluid being completely consumed and the flow regulator of FIG. 11B falling onto the fluid exit to stop the flow.

Referring to FIGS. 11 to 12, a disposable intravenous flow control device in accordance with a fifth preferred embodiment of the invention is shown. The characteristics of the fifth preferred embodiment are substantially the same as that of the fourth preferred embodiment except the following: The separation member is eliminated. The top of the suction cup 15A is a flat surface 151A. The neck 3220A has a convex longitudinal section and the groove 153A has a concave longitudinal section. The neck 3220A and the groove 153A can be complementarily engaged together. Bottom of the flow regulator 30A (i.e., the lower float member 32) is flat. Further, there is a distance between the annular member 152A and the bottom of the flow regulator 30A when the flow regulator 30A and the suction cup 15A are secured together.

Figures 13, 13A:
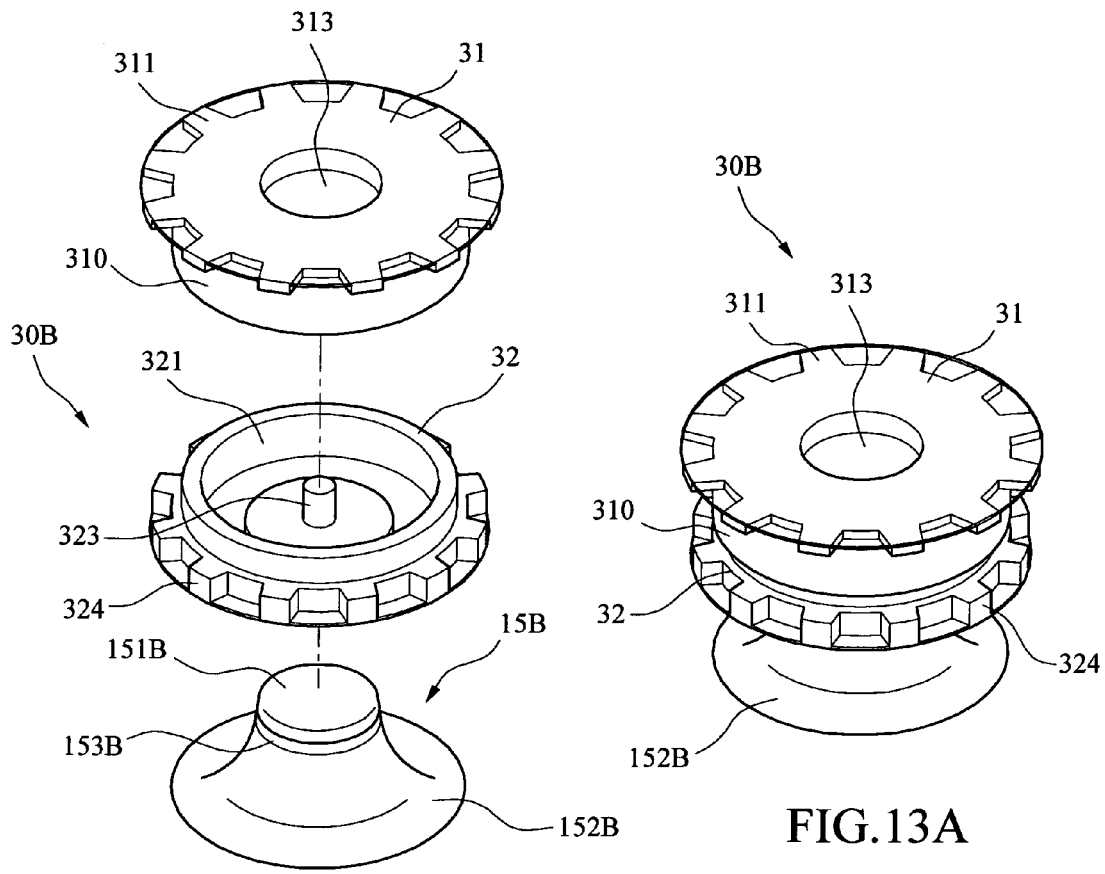
FIG. 13 is an exploded perspective view of a flow regulator as a part of a disposable intravenous flow control device according to a sixth preferred embodiment of the invention.
FIG. 13A is a perspective view of the assembled flow regulator of FIG. 13.
Figure 13B:
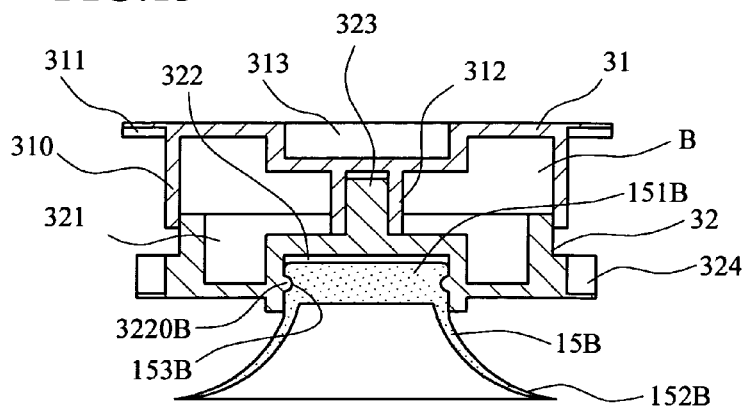
FIG. 13B is a longitudinal sectional view of the flow regulator of FIG. 13A.
Figure 14:
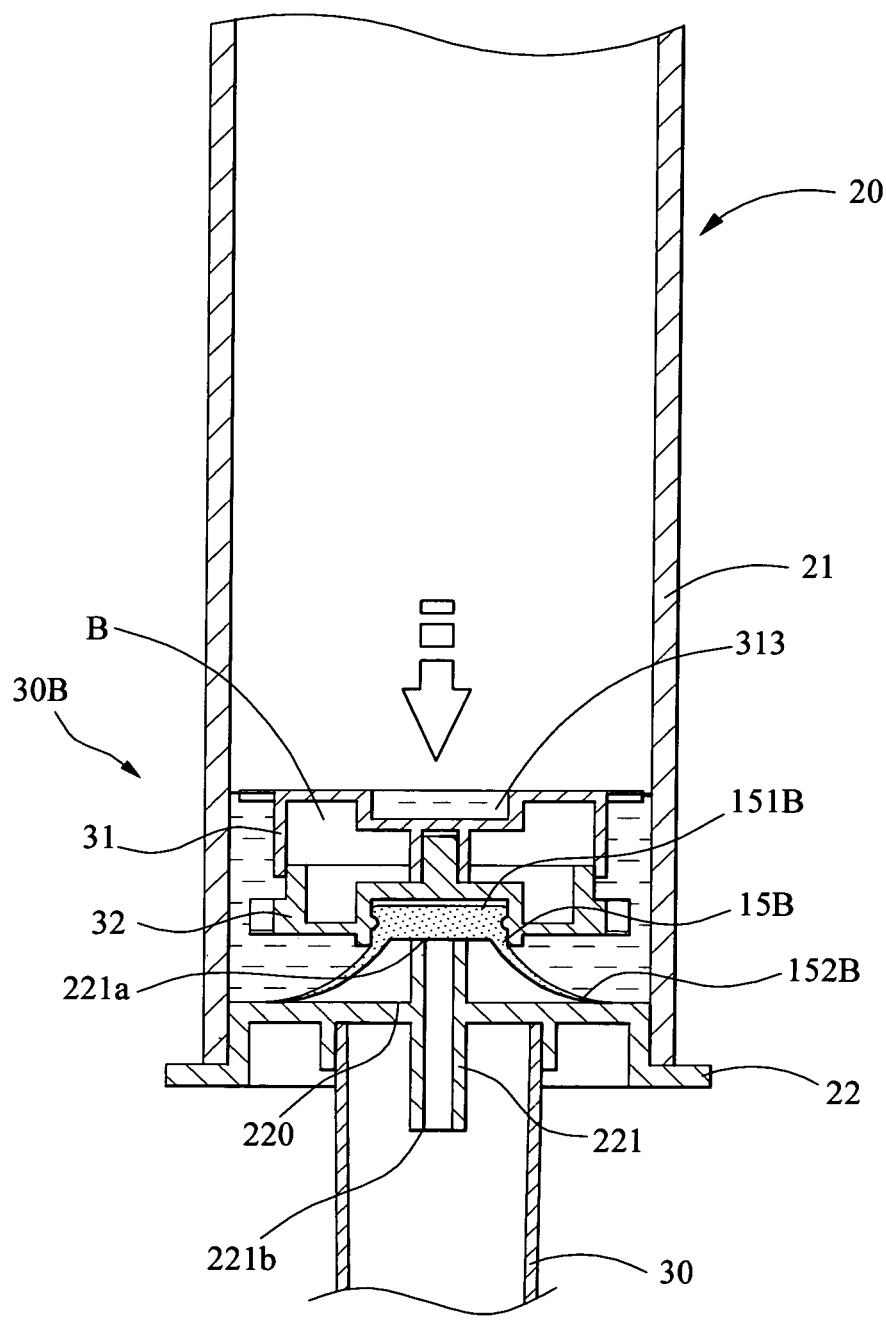
FIG. 14 is a view similar to FIG. 5A showing fluid being completely consumed and the flow regulator of FIG. 13B falling onto the fluid exit to stop the flow.
Figure 15:
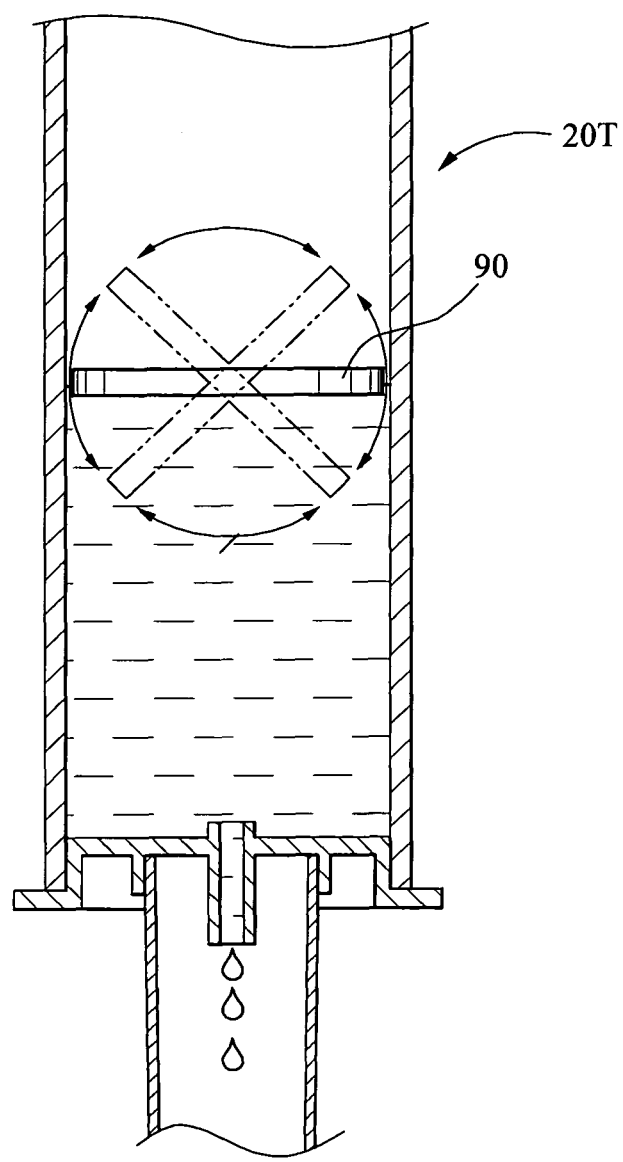
FIG. 15 is a longitudinal sectional view of important portions of a typical IV flow control device.

Referring to FIGS. 13 to 14, a disposable intravenous flow control device in accordance with a sixth preferred embodiment of the invention is shown. The characteristics of the sixth preferred embodiment are substantially the same as that of the fifth preferred embodiment except the following: Bottom of the flow regulator 30B (i.e., the lower float member 32) has an annular projecting rim. The suction cup 15B has a flared member 152B.

While the invention has been described in terms of preferred embodiments, those skilled in the art will recognize that the invention can be practiced with modifications within the spirit and scope of the appended claims.

What is claimed is:

1. A disposable intravenous flow control device (20) comprising:
   a rigid casing (21) defining a flow passage having a fluid entrance (23) and a fluid exit (22);
   a flow regulator (30, 30A, 30B) disposed in the flow passage of the casing (21) and comprising a disc-shaped upper float member (31) including a bottom outer rim (310), a plurality of equally spaced teeth (311) along an annular top edge, and a bottom inner rim (312); and a disc-shaped lower float member (32) including an annular flange (321) adjacent to an edge and extending upward, a solid cylinder (323) on the center of a top hollow riser (326), a plurality of equally spaced teeth (324) along the edge and below the flange (321), and a hollow cylindrical skirt (322) extending downward from the hollow riser (326) wherein the cylinder (323) is fitted in the inner rim (312) to secure the upper and lower float members (31, 32) together, and the outer rim (310) is securely engaged around the flange (321) so as to define a closed space (B) in the flow regulator (30); and
   a suction cup (15, 15A, 15B) releasably secured to the skirt (322) for blocking the fluid exit (22) when fluid in the casing (21) is consumed.

2. The disposable intravenous flow control device of claim 1, wherein the upper float member (31) further comprises a circular open fluid storage (313) on a top center.

3. The disposable intravenous flow control device of claim 1, wherein the suction cup (15) comprises a central, hollow projection (151) extending upward, a separation member (1511) for separating an internal space of the projection (151) into upper and lower portions, an annular groove (153) on an intermediate portion of an outer surface of the projection (151), and an annular member (152) on the bottom.

4. The disposable intravenous flow control device of claim 1, wherein the suction cup (15A) comprises a flat top surface (151A), an annular groove (153A) below the top surface (151A), and an annular extension member (152A) descending downward from the bottom of the groove (153A).

5. The disposable intravenous flow control device of claim 1, wherein the suction cup (15B) comprises a flat top surface (151A) (151B) lockingly fitted in the skirt (322), an annular groove (153B) below the top surface (151B), and a flared member (152B) depending downward from the groove (153B), and wherein the top surface (151B) has a thickness greater than that of the flared member (152B).

6. The disposable intravenous flow control device of claim 1, wherein buoyancy of the upper float member (31) is slightly greater than that of both the lower float member (32) and the suction cup (15, 15A, 15B).

7. The disposable intravenous flow control device of claim 6, wherein the specific weight of the flow regulator (30, 30A, 30B) is about 0.8 to 1.0.

8. The disposable intravenous flow control device of claim 6, wherein capacities of the fluid storage (313) and that of a closed space (B) defined by the outer rim (310) tightly engaged around an upper portion of the flange (321) are devised to be an optimum by taking the specific gravity of the fluid to be dispensed by the IV flow control device (20) into consideration.

* * * * *